United States Patent [19]
Yng-Wong

[11] Patent Number: 5,807,554
[45] Date of Patent: Sep. 15, 1998

[54] HERBAL FORMULATIONS WITH NACRE

[76] Inventor: Quing Non Yng-Wong, 5524 MacArthur Blvd., Washington, D.C. 20016

[21] Appl. No.: 835,959

[22] Filed: Apr. 11, 1997

[51] Int. Cl.$^6$ .................................................. A01N 65/00
[52] U.S. Cl. ...................... 424/195.1; 424/439; 424/464; 424/451; 424/422; 623/16
[58] Field of Search ................................. 424/195.1, 439, 424/464, 451, 422; 623/16

[56] References Cited

U.S. PATENT DOCUMENTS

| | | |
|---|---|---|
| 5,320,844 | 6/1994 | Liu . |
| 5,424,331 | 6/1995 | Shylankevich . |
| 5,425,769 | 6/1995 | Snyders . |
| 5,563,124 | 10/1996 | Damien et al. . |

FOREIGN PATENT DOCUMENTS

009308265A2  4/1993  WIPO .

OTHER PUBLICATIONS

Table reporting Clinical Data Using Pearl Powder (1996). Listing of Traditional Chinese Medicine use of marine calcium, extracted from Chinese Herbal Patent Formulas, Jake, 1986, Institute for Traditional Medicine.

Chinese Herbal Medicine, Bensky et al, Eastland Press, 1986, pp. 190, 191, 450–454, 477, 478, 504, 505, 577.

Giles et al, "Inorganic Overgrowth of Aragonite on Molluscan . . . ", Biol. Bull. 188: 8–15 (Feb./Mar. 1995), pp. 8–15.

McCabe, Jr. et al, "Calcium–Dependent Cell Death", Annals New York Academy of Sciences; Nov. 21, 1992.

Aiken et al, "A Peroxidative model of human erythrocyte . . . ",, Biochimica et Biophysica Acta 1270 (1995) 52–57.

Chinese Herbology by Dharmananda, Institiute for Traditional Medicine and Preventive Health Care, 1992, pp. 120, 194, 236, 240, 258, 359, 454.

*Primary Examiner*—Thurman K. Page
*Assistant Examiner*—Brian K. Seidleck
*Attorney, Agent, or Firm*—Nixon & Vanderhye P.C.

[57] ABSTRACT

Various complex formulations including the nacre form of calcium as a primary constituent are provided for dealing with a number of human ailments including insomnia, skin inflammation and itching, and anxiety disorders, and for increasing bone density. For bone density increase nacre is the main constituent, but the complex also includes sources of plant and/or animal collagen. The other compositions include nacre along with herbs to facilitate use of the nacre for treatment of various ailments or conditions.

21 Claims, No Drawings

HERBAL FORMULATIONS WITH NACRE

BACKGROUND AND SUMMARY OF THE INVENTION

Nacre (also known as Pearl Powder, Concha Margarita, Amber Poria Pearl, Concha Margaritaferae, marine calcium, and Mother of Pearl) is an excellent source of calcium and has been used by generations of Chinese to soothe restlessness, anxiety, and stress. It has been used with children, even newborn infants, to calm or cure seizures, epileptic episodes, and brain functions. It is also used with adults for these same conditions and also for senile memory problems.

Western laboratory sciences have tracked neurotransmission to the molecular level of electron exchanges. Calcium is central in receiving and sending signals from one nerve cell to another. The balance of calcium within the nerve cell is crucial to maintaining the health of the cell, the life or death of the cell. Calcium helps maintain the electrical energy capacity within the appropriate range for the specific nerve cells and helps absorb and eject toxins when they enter a cell. It is not surprising, then, that the health of the calcium transport system at the cellular level in nerve cells both reflects the health of the body as whole and affects the capacity of the body to withstand injury, invasion and stress. In 1993, Chinese laboratory research found memory improved because acetylcholinesterase activity was inhibited with nacre based formulae.

Calcium utilization, however, is low compared with calcium intake in the normal U.S. diet. Until recent identification of the preference of amino acids for nacre over other sources of calcium there has been no satisfactory explanation for this. One likely reason amino acids prefer nacre as their source of calcium was identified in Chinese laboratory research which identified amino acids as proportionately high in nacre. This makes it easy for alien amino acids to be attached to and to utilize nacre as a source of calcium and is an advantage other inorganic calcium sources cannot provide.

In the late 1960s Western psychiatry made a significant breakthrough with the discovery that lithium can combat uni-polar depression and, later, bipolar disease. This turned attention to the possibility that many psychological, emotional, behavioral problems are related to metabolism and, in particular, to metabolism of a few elements in the brain and central nervous system. While lithium is an effective treatment for various neurochemical imbalances and their psychological symptoms, it also affects other systems of the body, placing a strain on kidneys and other organs. For this reason, exploration of elements with similar chemical interactions as possible replacements for or alternatives to lithium began. Calcium has been the primary element which shares many of the chemical affinities of lithium, produces similar psychological correction of imbalances and has fewer negative side-effects than lithium. There is, then, a consensus of opinions that from Western psychiatric research and oriental treatment practices that calcium, and partly calcium in the form of nacre, has effects of restoring metabolic balance, calming the restless and hyperactive, healing at the cellular and systemic levels of the central nervous system, and facilitating sending and receiving of nerve impulses.

In traditional Chinese medicine, nacre has also been used in formulae for bone disorders and the healing of fractures and for insomnia, as well as in formulae for the treatment of hyperactivity, seizures, childhood epilepsy, senility, and symptoms of aging. It is believed that calcium is involved in neurotransmission on the molecular level of electron exchanges. The balance of calcium within the nerve cell is crucial to maintaining the health of the cell, in maintaining the electrical energy capacity within a specific range and in absorbing and rejecting toxins. The health of the calcium transport system reflects the ability to withstand injury, invasion, and stress. Memory has been found to improve as acetylcholinesterase activity is inhibited with nacre-based formulae. (See Peterson, Christine. Nov. 21, 1992. Changes in Calcium's Role as a Messenger during Aging in Neuronal and Non neuronal Cells. Annals New York Academy of Sciences, Volume 663, pp. 279–293.) Aging and/or stress induced alterations in calcium homeostasis are suspected in the disruption of several hippocampal processes that correlate with learning and memory. In patients with Alzheimers, total cell calcium levels are markedly elevated. It has been suggested that free radical levels resulting from oxidative stress is responsible for many age-related degenerative changes due to increased intracellular calcium levels.

According to the present invention, nacre is used as the primary constituent in a number of different formulas which are specific to improving the functionality of various human body parts, as well as providing relief for a number of different ailments and conditions, such as insomnia and anxiety. The formulations according to the present not only take advantage of nacre's ability to facilitate and maintain human health, but provide important additional constituents and functions which enhance the effectiveness of nacre for performing its intended functions and/or dealing with other aspects of the ailments or conditions to be corrected. The formulations according to the present invention are basically herbal in nature, have few or no side effects, and can be taken for long periods of time if necessary. They are also relatively simple and easy to produce and utilize.

According to one aspect of the present invention a formula is provided which is pharmacologically active in the relief of insomnia, anxiety, pain, and muscular tension, improving the quality of sleep in general. Such a formulation can have significant practical benefits for large segments of the population.

The number of people with chronic sleep deprivation has dramatically increased over the last two decades; in fact recent estimates suggest that as many as 40 million people in the U.S. may suffer from chronic or intermittent sleep disorders. Lack of sleep lowers the immune system and negatively affects brain functioning. During the 1990s the second leading cause of traffic accidents in the United States has been drivers falling asleep at the wheel. Lowered immunity increases the number and severity of minor illnesses as well as increasing susceptibility to major illnesses. In the last four years, studies have linked sleep cycle disruptions with a number of cancers. Physiologically, the causes of simple insomnia are primarily neurological. Lack of sleep quickly results in lowered brain function and altered brain chemistry.

The sleep facilitating formula according to the present invention has its basis in regulating calcium metabolism through the use of nacre. Calcium is a core mechanism through which nerve cells communicate. Calcium's metabolism is altered under stress, neurodegenerative diseases and in the aging process. Aging and/or stress-induced alterations in calcium homeostasis are suspected to disrupt processes in the hippocampus region of the brain. Nacre's effect parallels drugs that promote calcium uptake (calcium channel blockers), partially reversing deficits in calcium dependent processes.

The sleep facilitating formulation according to the present invention has nacre as the primary constituent thereof, typically between about 65–75% by weight (e.g. about 70% by weight). Two other ingredients are also provided. Sclerotium Poriae cocos is used to calm the mind and to regulate urination and edema. It assists in the actions of promoting sleep. Succinum is used as a second assistant to nacre for insomnia and also acts as a tranquilizing agent. Succinum and Sclerotium Poriae cocos are each preferably provided in the amount of about 13–17%, preferably about 15% by weight.

Another formulation according to the present invention is provided primarily to increase bone density, for preventing osteoporosis, and like disorders. However this formulation also relieves anxiety, pain, and muscular tension when administered in a pharmacologically effective amount for increasing bone density, and because of its nacre base can also improve the quality of sleep.

Currently, 25 million women in the United States are affected by osteoporosis. Osteoporosis leads to 1.5 million fractures each year. Annual medical care costs for fractures among older adults ranged from $7 to $10 billion in 1986 to $13.8 billion in 1995. The cost of osteoporosis is growing rapidly in human, medical and financial terms, especially in countries with aging populations. The number of persons 65 and older is projected to increase from 32.0 million to 51.5 million during 1990–2020. The formulation according to the invention is an alterative to current treatments, including controversial hormone replacement therapy (HRT), expensive drugs with serious side effects such as Fosamex, and calcium supplementation. Most forms of calcium are not well-utilized by the body; most of the calcium is simply excreted. The nacre-based formulation according to the invention is found to be most utilized by amino acids, the means by which the body metabolizes calcium. Nacre, when grafted on broken bones, stimulates new bone growth with the nacre matrix nearly indistinguishable from the matrix of human bone. Collagen is also necessary for bone growth. Sources of collagen in the typical American diet are few. It occurs in bones, sharks, a few ocean animals, and some plants not normally part of the U.S. diet. The formula of the invention thus desirably contains plant and animal based collagen.

The bone density increasing formulation according to the present invention has nacre as the primary constituent thereof, preferably between about 65–75% (e.g. about 71 %) by weight. Preferably at least about 5% collagen is also provided, about 4–6% of which is animal collagen such as Gelatinum asini, and about 1.5–2.5% of which is plant collagen, e.g. kudzu. Other ingredients are also provided.

Of the other ingredients in the bone formulation according to the invention besides nacre, the following beneficial affects can be expected: Angelicae sinensis radix nourishes the blood and promotes blood circulation. Gelatinum asini (a collagen source), glue made from ass's skin, also nourishes the blood and, in experiments on animals, was able to increase the absorption and utilization of calcium carbonate. Drynariae rhizoma, aka Rhizoma Gusuibu, assists and promotes the mending of sinews and bones (the Chinese name translates to "Mender of Shattered Bones"). Carthami tinctorii flos is also used as an agent to promote blood circulation. Paeonea rubrae radix (kudzu) is another agent for vitalizing the blood, i.e. a source of collagen. Psoraleae corylifoliae fructus is used for weakness of the back (the Chinese name translates to "Resin that Tonifies the Bone"). Pueraria radix is used to loosen tightness in the upper back and neck. Radix Panacis Quinqueofolii, aka American Ginseng, is used as a stimulant to the central nervous system; that is it is used in stress syndromes and helps promote calcium absorption.

According to another aspect of the present invention a skin formula is provided which has specifically beneficial affects on the health and appearance of hair, skin and nails. Because nacre is the majority component thereof it also has the effect of relaxing upper body tension (especially in the neck, shoulders, face and head) and has a calming affect on both the nervous and muscular systems. Nacre has historically been used in Chinese preparation, both topical and oral, for acne and other skin problems, and the composition according to the present invention contains kudzu and Radix Notoginseng to have a wide variety of beneficial affects for skin problems, including reducing inflammation, causing rashes to reduce in size or disappear, moistening skin, and relieving itching.

Another formulation according to the present invention contains nacre as a significant component, but not a majority component, thereof, and is useful for anxiety disorders. This "anxiety" formulation was originally developed for withdrawal symptoms encountered by persons going through rehabilitation of cocaine or heroin addiction. However it has now been found to be pharmacologically effective in relieving anxiety disorders and related problems.

Anxiety disorders are quite common, affecting from 5% to 10% of the general population. Many psychological, emotional and behavioral problems are related to the metabolism of a few elements in the central nervous system (CNS). Calcium metabolism has been under study in its effect on psychological well-being and correction of neurochemical imbalances. There is a growing consensus of Western psychiatric research and Chinese herbal treatment practices that calcium, particularly calcium in the form of nacre, has the effect of restoring metabolic balance, calming the CNS, and healing at the cellular level.

The anxiety formula according to the present invention has "Adaptogens" which help the body deal with stress. By harmonizing body functions the formulation helps with symptoms of irritability, forgetfulness, and general malaise. A smooth muscle relaxer is also included for digestive problems and for constriction in the chest.

The major ingredients of the anxiety formula according to the present invention, and their usefulness in the formulation are: Fructus Schisandrae Chinensis: Acts as a tranquilizer. It is useful for chronic cough, dream disturbed sleep, and insomnia. Nacre: In this formula it is used to sedate the mind when fright or anger is easily provoked. Cortex Acanthopanais Gracilistyli: This is used when the normal flow of energy and blood are obstructed, especially in the treatment of long term illness. Pericarpium Citri Reticulatae: This is effective in the loss of appetite, fatigue, and tightness in the chest.

According to the present invention there thus are provided a number of highly desirable nacre-based formulations that can effectively treat a wide variety of human ailments or conditions.

According to one aspect of the present invention a method of increasing human bone density in a human in need of treatment is provided. The method comprises the step (a) of administering to the human in need of treatment an ingestible material that primarily comprises nacre, and also includes at least about 5% by weight of a source of animal, plant, or both animal and plant, collagen, in an amount effective to increase bone density. Step (a) is typically practiced by administering a formulation comprising about 65–75% nacre, about 4–6% of a source of animal collagen, and about 1.5–2.5% of a source of plant collagen. That is step (a) is practiced by administering a complex formulation comprising a pharmacologically effective mixture of the following, which may have the indicated percentages (expressed in weight percent):

| | |
|---|---|
| Margaritaferae, concha (nacre) | 65–75% (e.g. about 70%) |
| Angelicae sinensis radix | 5–7% (e.g. about 6%) |
| Gelatinum asini (aka Corii asini gelatinum) | 4–6% (e.g. about 5%) |
| Rhizoma Gusuibu (aka Drynariae Rhizoma) | 3–5% (e.g. about 4%) |
| Carthami tinctorii flos | 3–5% (e.g. about 4%) |
| Paeonea rubrae radix | 3–5% (e.g. about 4%) |
| Psoraleae corylifoliae fructus | 1.5–2.5% (e.g. about 2%) |
| Puerariae radix (kudzu) | 1.5–2.5% (e.g. about 2%) |
| Panacis quinquefolii radix (aka American Ginseng) | 1.5–2.5% (e.g. about 2%) |

According to another aspect of the present invention there is provided a pharmacologically effective composition comprising a mixture of Margaritaferae, concha (nacre), Angelicae sinensis radix, Gelatinum asini (aka Corii asini gelatinum), Rhizoma Gusuibu (aka Drynariae Rhizoma), Carthami tinctorii flos, Paeonea rubrae radix, Psoraleae corylifoliae fructus, Puerariae radix (kudzu), and Panacis quinquefolii radix (aka American Ginseng), in a pharmacologically effective amount. The percentages of the components therein preferably are as set forth above.

According to another aspect of the present invention there is provided a pharmacologically effective composition comprising at least 65% by weight nacre, and at least 5% by weight animal, plant, or animal and plant collagen.

According to another aspect of the present invention a method of eliminating or ameliorating skin conditions including inflammation, rashes, itching, and/or swelling in a human patient in need of treatment, comprising the step (a) of administering to the human patient in need of treatment an ingestible material that comprises a pharmacologically effective mixture of nacre, kudzu and radix notoginseng, in a pharmacologically effective amount. Step (a) may be practiced by administering a formulation having the active composition, expressed in approximate weight percent, consisting essentially of:

| | |
|---|---|
| Concha Margaritaferae (nacre) | 65–75% (e.g. about 70%) |
| Radix Pseudoginseng | 17–23% (e.g. about 20%) |
| Radix Puerariae (kudzu) | 8–12% (e.g. about 10%). |

The invention also relates to a pharmacologically effective composition comprising a mixture of Concha Margaritaferae (nacre), Radix Notoginseng, and Puerariae radix (kudzu), in a pharmacologically effective amount (preferably in the percentages as set forth above).

According to another aspect of the present invention there is provided a method of substantially eliminating or ameliorating insomnia or other sleeping disorder in a human patient, comprising the step (a) of administering to the human patient in need of treatment an ingestible material having active ingredients consisting essentially of: Concha Margaritaferae, Sclerotium Poriae cocos, and Succinum, in a pharmacologically effective amount. Step (a) is preferably practiced by administering a complex having the following active composition (and consisting essentially of the components listed):

| | |
|---|---|
| Concha Margaritaferae (nacre) | 65–75% (e.g. about 70%) |
| Sclerotium Poriae cocos | 12–18% (e.g. about 15%) |
| Succinum | 12–18% (e.g. about 15%) |

The invention also relates to a pharmacologically effective composition comprising a mixture of (e.g. consisting essentially of) Concha Margaritaferae (nacre), Sclerotium Poriae cocos, and Succinum, in a pharmacologically effective amount. The percentage contributions of each of the active ingredients preferably are set forth above.

According to still another aspect of the present invention a method of substantially eliminating or ameliorating an anxiety disorder in a human patient is provided, comprising the step (a) of administering to the human patient in need of treatment an ingestible material, in a pharmacologically effective amount, having active ingredients consisting essentially of Fructus Schisandrae Chinensis, Concha Margaritaferae (nacre), Cortex Acanthopanais Gracilistyli, and Pericarpium Citri Reticulatae. Step (a) is typically practiced by administering a complex consisting essentially of the following and having the following composition in weight percent: Fructus Schisandrae Chinensis 35–50% (e.g. about 42%)

| | |
|---|---|
| Fructus Schisandrae Chinensis | 35–50% (e.g. about 42%) |
| Concha Margaritaferae (nacre) | 20–30% (e.g. about 24%) |
| Cortex Acanthopanais Gracilistyli | 13–19% (e.g. about 16%) |
| Pericarpium Citri Reticulatae | 14–22% (e.g. about 18%) |

DETAILED DESCRIPTION OF THE PREFERRED EMBODIMENT

Nacre, forming the iridescent inner layer of mollusk shells, is a highly ordered microlaminate composite of crystals and biopolymers with a strength and fracture resistance far exceeding the mineral crystals themselves. Nacre's composite biomaterials consist of calcium carbonate ($CaCO_3$) in a matrix of proteins and glycoproteins with calcium binding properties. Because of the organic matrix in which nacre is formed, similar to the matrix of human bone, this form of calcium is more bioavailable than other sources. Nacre's calcium is preferentially taken up by amino acids in living systems. Nacre also is commonly referred to as Pearl Powder, Mother of Pearl, Amber Poria Pearl, Concha Margarita, marine calcium, and Concha Margaritaferae.

One of the nacre based formulations according to the present invention is a formulation that is particularly useful, in a pharmacologically effective amount, for improving the quality of sleep. The formulation relieves insomnia, anxiety, pain, and muscular tension. The preferred formulation according to the invention is as follows (expressed in weight percent):

| | |
|---|---|
| Concha Margaritaferae (nacre) | 65–75% (about 70%) |
| Sclerotium Poriae cocos | 12–18% (about 15%) |
| Succinum | 12–18% (about 15%) |

Sclerotium Poriae cocos is used to calm the mind and to regulate urination and edema. It assists in the actions of promoting sleep. Succinum is used as a second assistant to nacre for insomnia and also acts as a tranquilizing agent.

Clinical data indicating the usefulness of the sleep improving formulation according to the present invention is indicated in Table I. Each capsule used in the data reported in Table I had about 300 mg of active ingredient, consisting essentially of about 70% nacre, and about 15% each of Succinum and Sclerotium Poriae cocos.

Psoraleae corylifoliae fructus is used for weakness of the back (the Chinese name translates to "Resin that Tonifies the Bone"). Puerariae radix is used to loosen tightens in the

TABLE I

CLINICAL DATA

| Log Number # | Patient Age & Gender | Dosage | Treatment Duration | Presenting Symptoms | Resultant Effects | Side Effects |
|---|---|---|---|---|---|---|
| 10 | 36 years male | 2 capsules, evening | 1 month | insomnia | improved sleep | none |
| 14 | 12 years female | 1 capsule, evening | 3 weeks | insomnia, trouble getting to sleep | within 3 days she was sleeping much better | continued use caused grogginess |
| 17 | 17 years female | 2 capsules, evening | 1 month | sleep interrupted by hot flashes | decrease in frequency and intensity of hot flashes, sleep significantly deeper and more restful | none |

The bone formulation according to the present invention increases bone density. It also relieves anxiety, pain and muscular tension. The preferred formulation is as follows (listed in weight percent):

| | |
|---|---|
| Margaritaferae, concha (nacre) | 65–75% (e.g. about 71%) |
| Angelicae sinensis radix | 5–7% (e.g. about 6%) |
| Gelatinum asini (aka Corii asini gelatinum) | 4–6% (e.g. about 5%) |
| Rhizoma Gusuibu (aka Drynariae Rhizoma) | 3–5% (e.g. about 4%) |
| Carthami tinctorii flos | 3–5% (e.g. about 4%) |
| Paeonea rubrae radix | 3–5% (e.g. about 4%) |
| Psoraleae corylifoliae fructus | 1.5–2.5% (e.g. about 2%) |
| Puerariae radix (kudzu) | 1.5–2.5% (e.g. about 2%) |
| Panacis quinquefolii radix (aka American Ginseng) | 1.5–2.5% (e.g. about 2%) |

Angelicae sinensis radix nourishes the blood and promotes blood circulation. Gelatinum asini, glue made from ass's skin, also nourishes the blood and, in experiments on animals, was able to increase the absorption and utilization of calcium carbonate (it is a source of animal collagen). Drynariae rhizoma, aka Rhizoma Gusuibu, assists and promotes the mending of sinews and bones (the Chinese name translates to "Mender of Shattered Bones"). Carthami tinctorii flos is also used as an agent to promote blood circulation. Paeonea rubrae radix (kudzu) is another agent for vitalizing the blood, being a source of plant collagen.

upper back and neck. Radix Panacis Quinqueofolii, aka American Ginseng, is used as a stimulant to the central nervous system; that is it is used in stress syndromes and helps promote calcium absorption.

The kudzu is particularly useful as a source of collagen, as is the gelatinum asini, comprising plant and animal sources of collagen, respectively. The total amount of collagen, from these or related or equivalent sources, is at last 5% preferably about 6–9%.

The skin formulation according to the present invention has numerous beneficial affects on the health and appearance of hair, skin, and nails. For example it can reduce inflammation, promote hair and nail growth, make the skin more moist, relieve itching, and the like. It also relaxes upper body tension, especially in the neck, shoulders, face and head. The desirable constituents according to the invention are (in approximate weight percent):

| | |
|---|---|
| Concha Margaritaferae (nacre) | 65–75% (e.g. about 70%) |
| Radix Pseudoginseng | 17–23% (e.g. about 20%) |
| Radix Puerariae (kudzu) | 10–12% (e.g. about 10%). |

Utilizing the formulation according to the invention, containing about 70% nacre, about 10% kudzu, and about 20% radix pseudo ginseng, with each capsule containing approximately 300 mg of active ingredient, the clinical data in Table II has been gathered:

TABLE II

CLINICAL DATA

| Log Number # | Patient Agent & Gender | Dosage | Treatment Duration | Presenting Symptoms | Resultant Effects | Side Effects |
|---|---|---|---|---|---|---|
| 100 | 53 years female | 2 capsules, 2 bid | 3 months | sympathetic dystrophy of the hand | reduced inflammation; hair and nails growing faster; skin more moist | none |
| 103 | 64 years female | 2 capsules, 2 bid | 2 months | neck inflammation with pain | reduced inflammation of neck; improvement with aches, pain, stiffness, and swelling | none |
| 106 | 42 years | 2 capsules, | 2 months | stiff neck and | stiff neck and | none |

TABLE II-continued

CLINICAL DATA

| Log Number # | Patient Agent & Gender | Dosage | Treatment Duration | Presenting Symptoms | Resultant Effects | Side Effects |
|---|---|---|---|---|---|---|
| | female | 2 bid | | shoulder; muscular tightness in legs; difficulty sleeping | shoulders "released"; sleep is fine | |
| 107 | 44 years female | 1 capsule, 2 bid | 3 months | stiff neck; headaches; skin rash on back of arms | stiff neck is gone; headaches do not last as long and are much less intense | none |
| 110 | 7 years male | 2 capsules, 2 bid | 1 month | neurodermatitis | this has been the only thing that has helped with the itching | none |

An anxiety formulation according to the present invention also has been developed, which can be used as a tea or in capsules. A preferred formulations according to the present invention is (expressed in weight percent):

| | |
|---|---|
| Fructus Schisandrae Chinensis | 35–50% (e.g. about 42%) |
| Concha Margaritaferae (nacre) | 20–30% (e.g. about 24%) |
| Cortex Acanthopanais Gracilistyli | 13–19% (e.g. about 16%) |
| Pericarpium Citri Reticulatae | 14–22% (e.g. about 18%) |

This formulation harmonizes body functions, helps with symptoms of irritability, forgetfulness, and general malaise, and provides a smooth relaxer for digestive problems and for constriction in the chest. Schisandrae acts as a tranquilizer. It is useful for chronic cough, dream disturbed sleep, and insomnia. Nacre, in this formula, is used to sedate the mind when fright or anger is easily provoked. Cortex Acanthopanais Gracilistyli is used when the normal flow of energy and blood are obstructed, especially in the treatment of long term illness. Pericarpium Citri Reticulatae is effective in the loss of appetite, fatigue, and tightness in the chest. The formulation is particularly effective when given in a pharmacologically effective amount to one with an anxiety disorder.

Utilizing the formulation according to the invention, containing about 42% Fructus Schisandrae Chinensis, about 24% nacre, about 16% Cortex Acanthopanais Gracilistyli, and about 18% Pericarpium Citri Reticulatae administered in the form of a tea, the clinical data in data in Table III has been gathered:

TABLE III

CLINICAL DATA

| Log No. # | Patient Age & Gender | Dosage | Treatment Duration | Presenting Symptoms | Resultant Effects | Side Effects |
|---|---|---|---|---|---|---|
| 407 | 49 years female | 1 package of tea, daily | 9 days | pain in arms and hands; insomnia; "stressed out"; anxious | reduced stress level; improved sleep; improved energy level; reduced pain; better able to focus | none |
| 405 | 40 years female | 1 package of tea, as needed | 3 months | muscle contractions of the upper back, neck and shoulder; chest tightness and palpitations; jaw problems, rashes, nerve pain/neuralgia | worked wonderfully; improved palpitations; keeps energy level good and steady; relieved muscular tightness in the upper body; | none |

In all of the formulations discussed above the nacre is preferably in the form of a fine powder.

For all of the formulations according to the invention in addition to the nacre and active herbal (or related) ingredients, the complexes utilized according to the present invention may have any number of substantially inert ingredients which will vary depending upon the particular form by which the complex will be administered. Normally the complexes are administered in the form of ingestible tablets or capsules which are swallowed with water, although the complex active ingredients may be mixed with food or beverage items and eaten or drunk, may be in the form of a tea, or in extreme cases may be introduced directly into the bloodstream using a hypodermic needle, I.V., or the like. The dose may vary depending upon the size, age, and condition of the patient being treated and the particular percentages of components in the complex utilized, but normally between about 500–2000 mg of active complex is administered per day, with part of the total dose preferably taken at two or more different times during the day.

A typical manner of processing herbs to produce a complex according to the invention may be as follows, although a wide variety of different known processing techniques may be utilized depending upon the exact form of the material desired, and the availability of material or equipment:

The powder end product of the complex is typically a 1:1 extract. Testing of raw materials used is conducted using standard organoleptic, High performance Liquid Chromatography, and microbiologic methods. The solvent mixture used for extractions for herbs used in the complex is about 95% SDA-3C and about 5% potable water. SDA-3C is specifically denatured alcohol composed of 95% ethanol and 5% isopropyl. The extraction method is thermokinetic maceration, specifically about 180° F. for about three hours, plus warm up and cool down.

Following extraction, a sample is tested for the percentage of dissolved solids recovered. This is compared with the specified standards and, when necessary, the processing is continued until the standards are reached. The base material of the extract is marc; no rinse of the extracted powder is required. The miscella is distilled. The distilled total miscella is dehydrated onto the base material. This receives a final milling (1/32" screen) in a sanitary stainless mill, using a vacuum system to transport the product directly into the final containers. Samples are taken for quality control tests which are visual, taste, microbiologic and High Performance Liquid chromatography. Samples are also taken for permanent record. That material is readily made into tablets, or placed in ingestible capsules, e.g. about 300 mg per capsule. The nacre powder may be added at any time (but preferably near or at the end) and mixed thoroughly with the other ingredients.

Another possible technique is as follows:

The powder and end product of this formula is typically a 1:1 extract. Testing of raw materials used is conducted using standard organoleptic, High Performance Liquid Chromatography and microbiologic methods. The solvent solution is preferably about 95% SDA-3C and 5% water.

The herb components and the solvent are added together in the extract processor for processing. The supernatant liquid of solvent and solids is drained into the holding/settling tank where the volume is measured and the solids content is determined by analysis. Samples are drawn of both and liquid supernatant and sediment for microbiologic testing. The supernatant liquid is pumped through a 100 mesh liquid filter into the Sanitizing vessel. The liquid is processed for a minimum of four hours at the boiling temperature of about 178° F. The volume of the liquid is measured and a solids analysis is done. A sample is drawn for microbiologic testing. The liquid is pumped through a 100 mesh filter and sprayed into the vacuum dryer, using volume and solids data to adjust the product to the desired concentration for the finished product. The resulting material is dried. The processor is emptied into sanitary bulk bins or barrels and transported to milling. A pre-grind sample is drawn for biologic testing. The material is milled in a sanitary stainless steel milling system using a 1/16" screen. The material is unloaded from the mill system directly via Vac-u-Max collector into double lined 44 gallon fiber drums. A sample is drawn from each container for biologic testing. Typical microbiologic requirements are:

|  | Limits |
| --- | --- |
| Aerobes | max. 10,000/g |
| Coliform | negative |
| Salmonella | negative |
| E. Coli | negative |
| Yeast | max. 100/g |
| Mold | max. 100/g |

The nacre powder may be added at any time (preferably near or at the end) and mixed thoroughly with the other ingredients.

According to the present invention it is thus possible to provide a number of highly advantageous nacre-based formulations which can effectively treat a number of different ailments and conditions, to substantially eliminate or ameliorate the ailments and conditions, or at least their symptoms. While the invention has been herein shown and described in what is presently conceived to be the most practical and preferred embodiment thereof it will be apparent to those of ordinary skill in the art that many modifications may be made thereof within the scope of the invention, which scope is to be accorded the broadest interpretation of the appended claims so as to encompass all equivalent products and methods.

What is claimed is:

1. A method of increasing human bone density in a human in need of treatment, comprising the step (a) of administering to the human in need of treatment an ingestible material, selected from the group consisting essentially of ingestible tablets or capsules, mixtures with food or beverage items, a tea, and introduced directly into the blood stream using a hypodermic needle or I.V., said material primarily comprising nacre, and also including at least about 5% by weight of a source of animal, plant, or both animal and plant, collagen, in an amount effective to increase bone density.

2. A method of recited in claim 1 wherein step (a) is practiced by administering a formulation comprising about 65–75% nacre, about 4–6% of a source of animal collagen, and about 1.5–2.5% of a source of plant collagen.

3. A method as recited in claim 1 wherein step (a) is practiced by administering a complex formulation comprising a pharmacologically effective mixture of: Margaritaferae, concha, Angelicae sinensis radix, Gelatinum asini, Rhizoma Gusuibu, Carthami tinctorii flos, Paeonea rubrae radix, Psoraleae corylifoliae fructus, Puerariae radix, and Panacis quinquefolii radix.

4. A method as recited in claim 1 wherein step (a) is practiced by administering a complex formulation having the following composition expressed in weight percent:

| Margaritaferae, concha | 65–75% |
| --- | --- |
| Angelicae sinensis radix | 5–7% |
| Gelatinum asini | 4–6% |
| Rhizoma Gusuibu | 3–5% |
| Carthami tinctorii flos | 3–5% |
| Paeonea rubrae radix | 3–5% |
| Psoraleae corylifoliae fructus | 1.5–2.5% |
| Puerariae radix | 1.5–2.5% |

-continued

| Panacis quinquefolii radix | 1.5–2.5%. |

5. A pharmacologically effective composition comprising a mixture of Margaritaferae, concha, Angelicae sinensis radix, Gelatinum asini, Rhizoma Gusuibu, Carthami tinctorii flos, Paeonea rubrae radix, Psoraleae corylifoliae fructus, Puerariae radix, and Panacis quinquefolii radix, in a pharmacologically effective amount.

6. A composition as recited in claim 5 wherein the components of the mixture have the following active ingredients expressed in weight percent:

| Margaritaferae, concha | 65–75% |
|---|---|
| Angelicae sinensis radix | 5–7% |
| Gelatinum asini | 4–6% |
| Rhizoma Gusuibu | 3–5% |
| Carthami tinctorii flos | 3–5% |
| Paeonea rubrae radix | 3–5% |
| Psoraleae corylifoliae fructus | 1.5–2.5% |
| Puerariae radix | 1.5–2.5% |
| Panacis quinquefolii radix | 1.5–2.5%. |

7. A pharmacologically effective composition comprising at least 65% by weight nacre, and at least 5% by weight animal, plant, or animal and plant, collagen.

8. A method of ameliorating the skin conditions of inflammation, rashes, itching, and/or swelling in a human patient in need of treatment, comprising the step (a) of administering to the human patient in need of treatment an ingestible material that comprises a pharmacologically effective mixture of nacre, kudzu and radix pseudoginseng, in a pharmacologically effective amount.

9. A method as recited in claim 8 wherein step (a) is practiced by administering a formulation having the active composition thereof, expressed in approximate weight percent, consisting essentially of:

| Concha Margaritaferae | 65–75% |
|---|---|
| Radix Pseudoginseng | 17–23% |
| Radix Puerariae | 10–12%. |

10. A pharmacologically effective composition comprising a mixture of Concha Margaritaferae, Radix Pseudoginseng, and Puerariae radix, in a pharmacologically effective amount.

11. A composition as recited in claim 10 wherein the components of the mixture consist essentially of the following active ingredients expressed in approximate weight percent:

| Concha Margaritaferae | 65–75% |
|---|---|
| Radix Pseudoginseng | 17–23% |
| Radix Puerariae | 10–12%. |

12. A pharmacologically effective composition comprising a mixture of Concha Margaritaferae (nacre), Sclerotium Poriae cocos, and Succinum, in a pharmacologically effective amount.

13. A composition as recited in claim 12 wherein the components of the mixture consist essentially of the following active ingredients expressed in weight percent:

| Concha Margaritaferae | 65–75% |
|---|---|
| Sclerotium Poriae cocos | 12–18% |
| Succinum | 12–18%. |

14. A method of substantially ameliorating a sleeping disorder in a human patient, comprising the step (a) of administering to the human patient in need of treatment an ingestible material having active ingredients consisting essentially of: Concha Margaritaferae, Sclerotium Poriae cocos, and Succinum, in a pharmacologically effective amount.

15. A method as recited in claim 14 wherein step (a) is practiced by administering a complex that consist essentially of the following active composition in weight percent:

| Concha Margaritaferae | 65–75% |
|---|---|
| Sclerotium Poriae cocos | 12–18% |
| Succinum | 12–18%. |

16. A method of substantially ameliorating an anxiety disorder in a human patient, comprising the step (a) of administering to the human patient in need of treatment an ingestible material, in a pharmacologically effective amount, having active ingredients consisting essentially of Fructus Schisandrae Chinensis, Concha Margaritaferae (nacre), Cortex Acanthopanais Gracilistyli, and Pericarpium Citri Reticulatae.

17. A method as recited in claim 16 wherein step (a) is practiced by administering a complex having the following composition in weight percent:

| Fructus Schisandrae Chinensis | 35–50% |
|---|---|
| Concha Margaritaferae | 20–30% |
| Cortex Acanthopanais Gracilistyli | 13–19% |
| Pericarpium Citri Reticulatae | 14–22%. |

18. A method as recited in claim 16 wherein step (a) is practiced by administering a complex having the following composition in weight percent:

| Fructus Schisandrae Chinensis | about 42% |
|---|---|
| Concha Margaritaferae | about 24% |
| Cortex Acanthopanais Gracilistyli | about 16% |
| Pericarpium Citri Reticulatae | about 18%. |

19. A method as recited in claim 14 wherein step (a) is practiced to treat insomnia.

20. A method as recited in claim 15 wherein step (a) is practiced to treat insomnia.

21. A method of claim 1 wherein the delivery means for intravenous is in the form of a hypodermic needle.

* * * * *